(12) United States Patent
Meirom et al.

(10) Patent No.: US 7,217,849 B2
(45) Date of Patent: May 15, 2007

(54) METHOD FOR THE PREPARATION OF N-PROPYL BROMIDE

(75) Inventors: Aharon Meirom, Arad (IL); Arieh Kampf, Meitar (IL); Dmitri Grinberg, Beer-Sheva (IL); Mark Grinberg, deceased, late of Haifa (IL); by Sarina Grinberg, legal representative, Meitar (IL)

(73) Assignee: Bromine Compounds Ltd. (IL)

( * ) Notice: Subject to any disclaimer, the term of this patent is extended or adjusted under 35 U.S.C. 154(b) by 0 days.

(21) Appl. No.: 10/495,232

(22) PCT Filed: Nov. 11, 2002

(86) PCT No.: PCT/IL02/00900

§ 371 (c)(1),
(2), (4) Date: Nov. 10, 2004

(87) PCT Pub. No.: WO03/042138

PCT Pub. Date: May 22, 2003

(65) Prior Publication Data

US 2005/0065386 A1    Mar. 24, 2005

(30) Foreign Application Priority Data

Nov. 12, 2001  (IL) .................................. 146456

(51) Int. Cl.
*C07C 17/08* (2006.01)
*C07C 17/00* (2006.01)
(52) U.S. Cl. ..................................... 570/248; 570/246
(58) Field of Classification Search ............... 570/248, 570/246
See application file for complete search history.

(56) References Cited

U.S. PATENT DOCUMENTS 5,138,110 A * 8/1992 Segall et al. ................ 570/258
2002/0151447 A1* 10/2002 Henry ......................... 510/175

FOREIGN PATENT DOCUMENTS

EP    0 446 537 A1    9/1991

* cited by examiner

*Primary Examiner*—Karl Puttlitz
(74) *Attorney, Agent, or Firm*—Lerner, David, Littenberg, Krumholz & Mentlik, LLP

(57) ABSTRACT

A method is described for producing n-propyl bromide of a high degree of purity, which contains isopropyl bromide in an amount lower than 0.1% w/w, and usually lower than 0.05%. The method is characterized in that n-propanol is reacted with HBr which is in gas form, preferably dry, and which is in excess over the stoichiometric amount, wherein the excess HBr is at the end of the reaction in an aqueous solution formed from the reaction water. The invention further relates to N-propyl bromide of high purity, containing typically less than 500 ppm of isopropyl bromide.

12 Claims, No Drawings

METHOD FOR THE PREPARATION OF N-PROPYL BROMIDE

FIELD OF THE INVENTION

This invention relates to a method for the production of n-propyl bromide which provides said compound with a high degree of purity and in particular, with an extremely low content of isopropyl bromide.

BACKGROUND OF THE INVENTION

N-propyl bromide is a product which has considerable industrial importance, particularly as a solvent for cleaning and degreasing replacing ODS (such as: 1,1,1-TCE, CFC-113) used in precision cleaning electronic defluxing, metal cleaning, adhesives, coatings, products and solvent applications.

In principle, n-propyl bromide is the product of a reaction between hydrobromic acid HBr and n-propanol. However, depending on the way in which the reaction is carried out, the result may be unsatisfactory, e.g., as to conversion and purity of the product, and most particularly, because of the contamination with by-products, especially isopropyl bromide.

Schematically, the reaction is as follows:

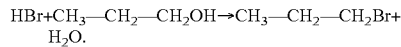

In prior art processes, the n-propyl bromide form contains a weight percentage of isopropyl bromide which may approach and even exceed 1%. (All the percentages in this specification and claims are by weight, unless otherwise indicated.) Said percentage is higher than desirable, because isopropyl bromide has a proven toxic effect, and it is a purpose of this invention to provide a process for the preparation of n-propyl bromide from HBr and n-propanol wherein the resulting n-propyl bromide contains amounts of isopropyl bromide equal or below 0.1%, preferably equal or below 0.05%, viz. equal or below 500 ppm.

It is another purpose of this invention to provide such a process which can be carried out continuously or in batch procedure.

It is a still further purpose of this invention to provide such a process which has a high conversion rate.

Other purposes and advantages of this invention will appear as the description proceeds.

SUMMARY OF THE INVENTION

The process for the production of n-propyl bromide according to the invention comprises reacting hydrogen bromide with n-propanol, and comprises feeding HBr which is in gas form and preferably dry. Water forms in the reaction and if an excess of HBr over the stoichiometric is fed, the excess HBr will be in an aqueous solution in the reaction water. According to a preferred feature of the invention, said aqueous solution should have, at the end of the reaction, a concentration of HBr not lower and preferably higher than 48%, and more preferably a concentration of 50–52%, or as high as 62%, viz. near saturation at room temperature. The molar excess of HBr required to achieve the desired final concentration of the HBr in aqueous solution can easily be determined by an easy stoichiomeric calculation. Generally, said excess may vary, e.g., from 20 mol % to 50 mol %, but these are not limitative values. The term "dry" in relation to HBr means in this application a content of water not higher than 1% w/w. The process of the invention, however, can be carried out with HBr that is in gas form but contains water in excess of 1% w/w.

The n-propanol may be liquid or gaseous. In one embodiment of the reaction—which is generally a batch process, but can be carried out continuously by feeding the reagents and withdrawing the product continuously—gaseous HBr is fed into liquid n-propanol, which is kept at the reaction temperature, which is not less than 40° C. and preferably, from 45 to 150° C. An aqueous phase and an organic phase are formed in the process and separate, the organic phase consisting of n-propyl bromide and the aqueous phase consisting of an HBr solution, at a weight concentration of HBr e.g. from 48 to 62%.

It should be understood that, in some embodiments of the process, portions of the aqueous phase may be separated as soon as formed, out of contact with the organic phase, and if so, the HBr concentration of such portions is not critical and may be lower than 48%.

In another embodiment of the invention, which is a continuous process, gaseous HBr and n-propanol vapors are fed to a reaction space—generally a column—in which a catalyst is present, and which is kept at a temperature above the boiling point of n-propanol, preferably above 100° C. The reaction product is discharged from the reaction space to a cold condenser. The condensed product again comprises an organic phase and an aqueous phase, which is an aqueous solution of HBr. The two phases are collected and allowed to separate. However, the separation occurs only after the end of the reaction, and therefore during the reaction the organic phase and the aqueous phase are always in contact and the concentration of the HBr solution must be within the limits herein specified.

The amount of isopropyl bromide in the reaction product, when the reaction is carried out according to the invention, is below 0.1%, usually considerably below 0.05 wt %, e.g., between 100 and 450 ppm. An n-propyl bromide having such a low amount of isopropyl bromide is not known in the art and is not achievable by the processes known in the art, and therefore, constitutes in itself an aspect of the invention.

As has been said, the process of the invention can be carried out in batch or continouosly.

The batch process is preferably performed in a stirred reactor equipped with a reflux condenser, a thermometer and a dip-pipe used for the addition of the HBr. Heating and cooling are supplied by a bath. It is also possible to circulate the contents of the reactor through a packed column in countercurrent to the HBr stream.

The continuous process is preferably performed in packed columns containing various brands of active carbon. Heating to the desired temperature is supplied to the upper two thirds of the column by an external heating tape. Two feed pipes, one for n-propanol and the other for HBr, are connected to the top of the column. The reagents are co-fed at calculated weight ratios, reacting while flowing downwards through the hot area to the lower cold area where they condense, to be collected in a cold vessel. Temperatures at various points along the column are measured with thermocouple probes.

DETAILED DESCRIPTION OF PREFERRED EMBODIMENTS

The following examples are illustrative and not limitative.

EXAMPLE 1

Batch Reaction Between 100% HBr Gas and N-propanol

N-propanol (120 Kg) is fed into a reactor and heated to 45° C. Gaseous HBr is fed at constant temperature during about 21 hours (at a rate of 11.4 Kg/hr and about 239 Kg). The molar ratio HBr/n-propanol is about 1.5:1. At the end of the HBr feeding period, the mixture is heated to 60–65° C. for an additional 2 hours, then cooled to ambient temperature. The two phases formed during the process are separated. N-propyl bromide (d=1.35) is the upper phase. The lower phase is a ~50% HBr solution in the reaction water, said solution having a density of 1.55. The two phases are separately discharged from the reactor. The upper, n-propyl bromide phase (170 liters), is evaporated and dried. Its content of isopropyl bromide, before evaporation, is 100–200 ppm. The lower 50% HBr solution phase has a volume of 90 liters. Though the solubility of n-propylbromide in such an aqueous solution is low, a small amount of n-propyl bromide is recovered by distillation from said solution.

The characteristics of the n-propyl bromide product are: GC: 99.8–99.9%; Water: 100–300 ppm; Color: 5 Apha; Isopropyl bromide: 200–300 ppm. Yield, based on n-propanol: 95%. The concentration of isopropyl bromide in the product is slightly higher than its concentration in the organic phase withdrawn from the reactor, because during the evaporation of the organic phase there are removed some impurities, such as dipropylether, some unreacted propanol and some heavy by-products.

EXAMPLE 2

Continuous Reaction Between 100% HBr Gas and N-propanol Vapor

Into the top of a column of 25 mm diameter and 33 cm length, packed with active carbon (F-300 by Chemviron), n-propanol vapors (above 100° C.) and 100% HBr gas are fed simultaneously at an 1:1.37 molar ratio respectively. The column is kept at an average temperature of 102–120° C. The rate of alcohol addition is 50 gr/hour. After two hours, the crude product (202 gr) contained less than 500 ppm of isopropyl bromide. Here an aqueous phase of 55% HBr is collected, along with the organic product. The n-propyl bromide is washed with water and neutralized. It should be noted that in the reaction in which propanol is in the gas phase, an excess of HBr significantly lower than that used when the propanol is liquid suffices to give the desired low isopropyl bromide percentage in the product. It is believed that this is due to the fact that the gases are cooled to ambient temperature as soon as they emerge from the reaction zone and no more isomerization to isopropyl bromide takes place.

Characteristics of the n-propyl bromide product: GC: 99.7%; Water: ND; Color: ND; Isopropyl bromide: 450 ppm; Yield, based on n-propanol: 98.1%.

EXAMPLE 3

Batch Reaction Between 100% HBr Gas and N-propanol Under Pressure n-Propanol (600 g) was fed into a 1.3 liter pressure reactor. Into the sealed reactor, HBr gas (100%, 1100 g) was fed at 80° C. The total addition time was 80 minutes. The pressure in the reactor rose to a maximum of 2.5 atm. The reactor was cooled to ambient temperature and the lower aqueous phase (464 g of 62% HBr) was separated. The organic phase was neutralized by washing with 20% sodium hydroxide, yielding n-propyl bromide (1210 g). Analysis: 99.7% n-propyl bromide, isopropyl bromide below 0.05%.

In the following comparative examples, aqueous solutions of HBr are used for the reaction with n-propanol. Examples 4, 5 and 6 are comparative examples. Examples 4 and 5 illustrate liquid phase reactions, and Example 6 a gas phase reaction not according to the invention, since the HBr is fed as an aqueous solution and not as a gas.

EXAMPLE 4

Batch Reaction Between 62% HBr Solution and N-propanol

Both liquids are fed into a reactor at ambient temperature (8034 Kg and 1269 Kg, respectively, molar ratio HBr/n-propanol 2.9:1.0). The stirred mixture is heated to 61–66° C. for 3 hours. After cooling, two phases are separated at 30° C. The lower phase consists of 48% HBr, in which a part of the product is dissolved. The upper phase consists of n-propyl bromide. The aqueous phase is heated up to 125° C. to recover the dissolved n-propyl bromide by evaporation. This fraction is combined with the main product.

The product is washed with alkali and dried over anhydrous sodium carbonate.

Characteristics of the n-propyl bromide product: GC: 99% min.; Water: 250 ppm; Color: 60 Apha; Isopropyl bromide: 0.14%. Yield, based on n-propanol: 96–97%.

EXAMPLE 5

Continuous Reaction Between 48% HBr Solution and N-propanol

A mixture of 48% HBr and n-propanol is heated in a stirred reactor to 122–123° C. More of both reagents is continuously fed via pumps in equimolar quantities, while removing simultaneously by distillation all the n-propyl bromide and water formed in the process. The concentration of the HBr is kept constant at 48% during the whole process. Thus, at an average rate of 4.5 Kg n-propanol/hour feeding (with parallel feeding of HBr), a crop of 345 Kg of n-propyl bromide was collected within ca. 37 hours of operation.

Characteristics of the n-propyl bromide product: GC: 98.2–98.7%; Water: ND; Color: ND; Isopropyl bromide: 0.6–1.1%; Yield, based on n-propanol: 95%.

EXAMPLE 6

Continuous Reaction Between 48% HBr and N-propanol in Gas Phase

Into the top of a column packed with active carbon (¾" diameter and 40 cm long), n-propanol vapors (at 100° C.) and vaporized 48% HBr (122° C.) are fed simultaneously at an equimolar ratio. The HBr feed is kept constant at 278 gr/hour of 48% solution. The product collected at the lower part of the column consists (after cooling) of two phases: the upper one is mainly the depleted HBr containing some unreacted n-propanol, and the lower, n-propyl bromide. The conversion based on n-propanol is about 90%, and that based on HBr is about 82%.

Characteristics of the n-propyl bromide product: GC: 97–99%; Water: 100–300 ppm; Color: ND; Isopropyl bromide: 0.8–1.6 wt %; Yield, based on n-propanol; 90%.

It is seen that when an aqueous solution of HBr is used, the product contains at least 0.14 wt % of isopropyl bromide and in most cases, more, e.g., up to 1.6 wt %. This occurs whether the reaction is carried out in batch form as a continuous reaction, and in this latter case whether the HBr solution is fed as such or is vaporized, and with different concentrations of aqueous HBr solution.

The following table illustrates the comparison between the process of the invention and the prior art.

| No. | Reagents | Phase | n-PrBr % | i-PrBr % |
|---|---|---|---|---|
| 1 | 100% HBr gas and n-propanol | liquid | 99.8 | 0.03 |
| 2 | 100% HBr gas and n-propanol | gas | 99.7 | 0.045 |
| 3 | 62% HBr and n-propanol | liquid | 99 | 0.5 |
| 4 | 48% HBr and n-propanol | liquid | 98–98.7 | 0.6–1.1 |
| 5 | 48% HBr and n-propanol | gas | 97–99 | 0.8–1.6 |

The catalyst used in the continuous gaseous reaction according to the invention may be different from the active carbon mentioned in Example 2. Other carbons or different catalysts can be used, e.g. RD3 or RB1 produced by Norit Nederland B. V. of 3800 Ac Amersfoort, The Netherlands, RB1 by Norit, granular activated carbon by Darco, F-300-Chemviron Carbon of Zoning Industriel C. de Feluy, B-7181 Feluy, Belgium. The temperature range can also vary. A wide range of temperatures may be used: 97–160° C. at atmospheric or superatmospheric pressure.

While embodiments of the invention have been described by way of illustration, it will be understood that the invention may be carried into practice with many modifications, variations and adaptations, without departing from its spirit or exceeding the scope of the claims.

The invention claimed is:

1. A process for the production of n-propyl bromide containing less than 0.1% isopropyl bromide by reacting hydrogen bromide (HBr) with n-propanol, comprising the steps of:
   i) feeding said n-propanol into a reactor;
   ii) feeding said HBr, in the form of a gas and in sufficient excess over the stoichiometric amount so as to produce an aqueous solution of HBr in the reaction water having a concentration of at least about 50%;
   iii) contacting said n-propanol with said HBr without removing water from the reaction mixture; and
   iv) cooling the reaction mixture and collecting the upper phase.

2. The process according to claim 1, wherein the HBr is dry.

3. The process according to claim 1, wherein said gaseous HBr is in a molar excess over the stoichiometric amount of at least 20% with respect to n-propanol.

4. The process according to claim 1, carried out as a batch process.

5. The process according to claim 4, carried out by feeding said gaseous HBr into said n-propanol in the form of a liquid.

6. The process according to claim 1, carried out as a continuous process.

7. The process according to claim 6, carried out by feeding said gaseous HBr and said n-propanol in the form of vapors to a reaction space, in which a catalyst is present and which is kept at a temperature above the boiling point of said n-propanol.

8. The process according to claim 1, wherein an inorganic phase and an organic phase are formed, the organic phase consisting of n-propyl bromide and the inorganic phase consisting of an HBr solution, and which process comprises cooling the reaction product and separating the two phases and recovering the n-propyl bromide.

9. The process according to claim 7, carried out in a reaction space, the temperature of said reaction space being above 100° C.

10. The process according to claim 7, wherein said catalyst is selected from the group consisting of active carbon and granular activated carbon.

11. The process of claim 1 further comprising the step of heating said reactor at a temperature of 45 to 150° C. prior to the addition of the HBr.

12. A process for the production of n-propyl bromide containing less than 0.05% isopropyl bromide by reacting hydrogen bromide (HBr) with n-propanol, comprising the steps of:
   i) feeding said n-propanol into a reactor;
   ii) feeding said HBr, in the form of a gas and in sufficient excess over the stoichiometric amount so as to produce an aqueous solution of HBr in the reaction water having a concentration of at least about 50%;
   iii) contacting said n-propanol with said HBr without removing water from the reaction mixture; and
   iv) cooling the reaction mixture and collecting the upper phase.

* * * * *

UNITED STATES PATENT AND TRADEMARK OFFICE
CERTIFICATE OF CORRECTION

PATENT NO. : 7,217,849 B2 Page 1 of 1
APPLICATION NO. : 10/495232
DATED : May 15, 2007
INVENTOR(S) : Aharon Meirom et al.

It is certified that error appears in the above-identified patent and that said Letters Patent is hereby corrected as shown below:

Column 5, line 8, delete "0.5" insert --0.14--.

Signed and Sealed this

Sixth Day of November, 2007

JON W. DUDAS
*Director of the United States Patent and Trademark Office*